US011885742B2

(12) United States Patent
Matsuda et al.

(10) Patent No.: US 11,885,742 B2
(45) Date of Patent: Jan. 30, 2024

(54) RECEIVER, DETECTION SYSTEM, AND DETECTION METHOD

(71) Applicant: NEC Corporation, Tokyo (JP)

(72) Inventors: Yuma Matsuda, Tokyo (JP); Akihiro Tanaka, Tokyo (JP)

(73) Assignee: NEC CORPORATION, Tokyo (JP)

(*) Notice: Subject to any disclaimer, the term of this patent is extended or adjusted under 35 U.S.C. 154(b) by 111 days.

(21) Appl. No.: 17/440,382

(22) PCT Filed: Jan. 27, 2020

(86) PCT No.: PCT/JP2020/002766
§ 371 (c)(1),
(2) Date: Sep. 17, 2021

(87) PCT Pub. No.: WO2020/195102
PCT Pub. Date: Oct. 1, 2020

(65) Prior Publication Data
US 2022/0155224 A1 May 19, 2022

(30) Foreign Application Priority Data
Mar. 26, 2019 (JP) ................................. 2019-058455

(51) Int. Cl.
G01N 21/59 (2006.01)
G01J 3/42 (2006.01)
(Continued)

(52) U.S. Cl.
CPC ............... *G01N 21/59* (2013.01); *G01J 3/42* (2013.01); *G01N 21/534* (2013.01); *G01N 33/0027* (2013.01); *G08B 17/10* (2013.01)

(58) Field of Classification Search
CPC .. G01N 21/59; G01N 21/534; G01N 33/0027; G01N 21/255; G01N 21/3504;
(Continued)

(56) References Cited

U.S. PATENT DOCUMENTS

2002/0075910 A1 6/2002 Imaki et al.
2004/0125374 A1* 7/2004 Berger ....................... G01J 3/18
356/364

(Continued)

FOREIGN PATENT DOCUMENTS

JP H04-212727 A 8/1992
JP H07-098252 A 4/1995
(Continued)

OTHER PUBLICATIONS

International Search Report for PCT Application No. PCT/JP2020/002766, dated Apr. 7, 2020.
(Continued)

*Primary Examiner* — Md M Rahman

(57) ABSTRACT

A receiver comprises: optical signal distributing means for distributing an optical signal transmitted to detect a detection target on a traveling path to two or more paths; a detection unit configured to detect a received light intensity of the optical signal at a first position where the received light intensity increases when the optical axis is shifted and at a second position where the received light intensity decreases; an intensity ratio calculation unit configured to calculate a ratio between the received light intensity at the first position and the second position based on the output of the detection unit; and a determination unit configured to determine whether or not there is an optical axis shift based on a change in the ratio of the received light intensity calculated by the intensity ratio calculation unit.

14 Claims, 21 Drawing Sheets

(51) Int. Cl.
*G01N 21/53* (2006.01)
*G01N 33/00* (2006.01)
*G08B 17/10* (2006.01)

(58) Field of Classification Search
CPC . G01J 3/42; G01J 3/027; G01J 3/0289; G08B 17/10; G08B 29/20; G08B 17/103
USPC ........................................... 356/432
See application file for complete search history.

(56) References Cited

U.S. PATENT DOCUMENTS

| | | | | |
|---|---|---|---|---|
| 2007/0009098 | A1* | 1/2007 | Tanaka | H04L 9/0858 380/30 |
| 2008/0052577 | A1* | 2/2008 | Tanaka | H04L 9/0838 714/728 |
| 2010/0195831 | A1* | 8/2010 | Tanaka | H04L 9/0858 380/279 |
| 2017/0131204 | A1* | 5/2017 | Sieben | G01N 21/0332 |
| 2019/0296519 | A1 | 9/2019 | Kassi | |
| 2019/0391073 | A1 | 12/2019 | Tanaka | |

FOREIGN PATENT DOCUMENTS

| | | | |
|---|---|---|---|
| JP | H07-280513 A | 10/1995 | |
| JP | H07-280951 A | 10/1995 | |
| JP | H10-214546 A | 8/1998 | |
| JP | H10-253329 A | 9/1998 | |
| JP | 2001-076325 A | 3/2001 | |
| JP | 2002-237651 A | 8/2002 | |
| JP | 2004-275504 A | 10/2004 | |
| JP | 2012-164112 A | 8/2012 | |
| JP | 6930548 B2 * | 9/2021 | ............. G01J 3/027 |
| WO | 2018/060285 A1 | 4/2018 | |
| WO | 2018/139412 A1 | 8/2018 | |

OTHER PUBLICATIONS

Iseki Takaya., "Trace Gas Detection Technique Using Near Infrared Semiconductor Laser", Journal of the Japan Society of Mechanical Engineers, vol. 107, No. 1022 (2004). pp. 51.

H. Saito et al., "Measurement of atmospheric carbon dioxide by applying differential absorption spectroscopy in the near infrared region", 31st Laser Sensing Symposium, D-3 (2013), pp. 1-4.

Yasuyuki Kamimura et al., "Optical measuring technology using quadrant photocells", Seisan Kenkyu, vol. 45, No. 12, Dec. 1, 1993, pp. 44-51.

JP Office Action for JP Application No. 2022-18628, dated Sep. 12, 2023 with English Translation.

* cited by examiner (A)

(B)

(A)

(B)

(A)

(B)

(C)

(D)

RECEIVER, DETECTION SYSTEM, AND DETECTION METHOD

This application is a National Stage Entry of PCT/JP2020/002766 filed on Jan. 27, 2020, which claims priority from Japanese Patent Application 2019-058455 filed on Mar. 26, 2019, the contents of all of which are incorporated herein by reference, in their entirety.

TECHNICAL FIELD

The present invention relates to a receiver, a detection system and a detection method, and more particularly to a technique for detecting an optical axis shift of an optical signal.

BACKGROUND ART

A detection system using a wide area sensor has been proposed. The system transmits an optical signal to a space and monitors the generation of smoke or gas due to abnormal conditions such as fires. The detection system detects the generation of smoke or gas based on the amount of decrease in a received light intensity from an initial state. Here, the initial state is a state in which no gas or smoke is generated.

However, in operation for a long period of time, an optical axis may be shifted due to vibration or impact from the external environment. In this case, if the received light intensity decreases due to the optical axis shift, an increase in the concentration of gas or smoke may be erroneously detected.

Therefore, when an optical axis shift occurs, it is necessary to quickly detect the shift. It is necessary to separate the optical axis shift from the received light intensity decrease due to gas or smoke, since the received light intensity decreases when smoke is generated.

Patent Literature 1 discloses a technique for monitoring the generation of smoke by using one main light emitting element and two or more sub light emitting elements arranged around the main light emitting element. When the dimming rate of the light received at the main light emitting element becomes greater than or equal to a threshold value, the main light emitting element is turned off, and two or more sub light emitting elements are sequentially turned on. When the dimming rates of all the light received by the light emitting elements exceed the threshold value, it is determined that smoke exists, and when only a part of the dimming rates of the light received by the light emitting elements exceed the threshold value, it is determined that an optical axis shift exists.

An optical method for detecting a gas utilizes the property that the gas to be detected absorbs light having a wavelength inherent to the substance. In general, there are two methods for calculating the gas concentration.

The first method uses a narrow wavelength band light source that outputs a wavelength near the absorption wavelength and modulates the wavelength to detect gas. Non-Patent Literature 1 discloses a gas detection technique by wavelength modulation spectroscopy (WMS).

The second method is to calculate the gas concentration from a known spectral intensity using a light source having a wide wavelength band. Non-Patent Literature 2 discloses a technique for detecting gas by differential absorption spectroscopy (DOAS: Differential Optical Absorption Spectroscopy).

CITATION LIST

Patent Literature

Patent Literature 1: Japanese Unexamined Patent Application Publication No. 2012-164112

Non Patent Literature

Non-Patent Literature 1: Takaya Iseki, "Trace Gas Detection Technology Using Near Infrared Semiconductor Laser," Journal of the Japan Society of Mechanical Engineers, Vol. 107, No. 1022, p. 51, 2004

Non-Patent Literature 2: Hayato Saito, et al., "Measurement of atmospheric carbon dioxide by applying differential absorption spectroscopy in the near infrared region" the 31st Laser Sensing Symposium D-3, 2013

SUMMARY OF INVENTION

Technical Problem

In a wide-area sensor for spatially propagating an optical signal, there has been a problem that an optical axis shift cannot be detected under a situation where the received light intensity is reduced by gas, smoke, dust, etc.

According to the method of Patent Literature 1, when a part of the light emitting elements receives light less than the threshold value, it is determined that there is an optical axis shift. Therefore, when all the light emitting elements receive light less than the threshold value, the optical axis shift cannot be detected. Therefore, in an environment where the received light intensity is reduced, the optical axis shift cannot be detected by the method of Patent Literature 1.

An object of the present disclosure is to provide a receiver, a detection system, and a detection method capable of detecting an optical axis shift under an environment where the received light intensity fluctuates.

Solution to Problem

A receiver according to the present disclosure comprising:
optical signal distributing means for distributing an optical signal transmitted for detecting a detection target on a traveling path to two or more paths;
detection means for detecting a received light intensity of the optical signal at a first position where the received light intensity increases when the optical axis of the optical signal is shifted and at a second position where the received light intensity decreases when the optical axis is shifted;
intensity ratio calculation means for calculating the ratio of the received light intensity at the first position and the received light intensity at the second position based on the outputs of the detection means;
determination means for determining the presence or absence of an optical axis shift based on a change in the light intensity ratio calculated by the intensity ratio calculation means.

The detection system according to the present disclosure comprising:
the receiver; and
a transmitter for transmitting the optical signal, wherein the detection system detects the detection target on the traveling path of the optical signal transmitted from the transmitter.

The detection method according to the present disclosure including:

distributing an optical signal in two or more paths;
receiving the distributed optical signals at a first position where the received light intensity increases when the optical axis of the optical signal is shifted and at a second position where the received light intensity decreases when the optical axis is shifted;
calculating a received light intensity ratio based on the signal intensity at the first position and the signal intensity at the second position;
determining the presence or absence of an optical axis shift based on a change in the received light intensity ratio.

Advantageous Effects of Invention

According to the present disclosure, even in an environment where the received light fluctuates, it is possible to detect an optical axis shift based on the ratio between the received light intensities at the plurality of detection positions. This is because even in an environment where the received light intensity fluctuates, the received light intensities change at the same rate, and the ratio becomes constant.

BRIEF DESCRIPTION OF DRAWINGS

FIG. 11 B shows the light receiving surface and the profile of an optical signal with a large optical axis shift in the general capture and tracking technique used in optical communication systems.

FIG. 13 B is a graph showing a change in the received light intensity of a detector 2 when the optical axis is shifted at time t according to an embodiment of the second invention.

FIG. 16 B is a graph showing a change in the received light intensity of a sub-detector 1 with time when the optical axis is shifted at time t according to the third embodiment.

FIG. 16 C is a graph showing a change in the received light intensity of a sub-detector 2 with time when the optical axis is shifted at time t according to the third embodiment.

FIG. 16 D is a graph showing a change in the received light intensity of a sub-detector 3 with time when the optical axis is shifted at time t according to the third embodiment.

FIG. 17 B is a graph showing a change in the received light intensity ratio between the sub-detector 2 and the main detector when the optical axis is shifted at time t according to the third embodiment.

FIG. 17 C is a graph showing a change in the received light intensity ratio between the sub-detector 3 and the main detector when the optical axis is shifted at time t according to the third embodiment.

FIG. 18 B shows the initial optical axis position (B) of an optical signal incident on a photodetector according to a typical capture and tracking technique.

FIG. 18 C shows an example (C) of optical axis positions of optical signals incident on detectors according to the third embodiment when there is an optical axis shift.

FIG. 18 D shows an example (D) of an optical axis position of an optical signal incident on a detector according to the typical capture and tracking technique when there is an optical axis shift.

DESCRIPTION OF EMBODIMENTS

First Embodiment

Figure 1:
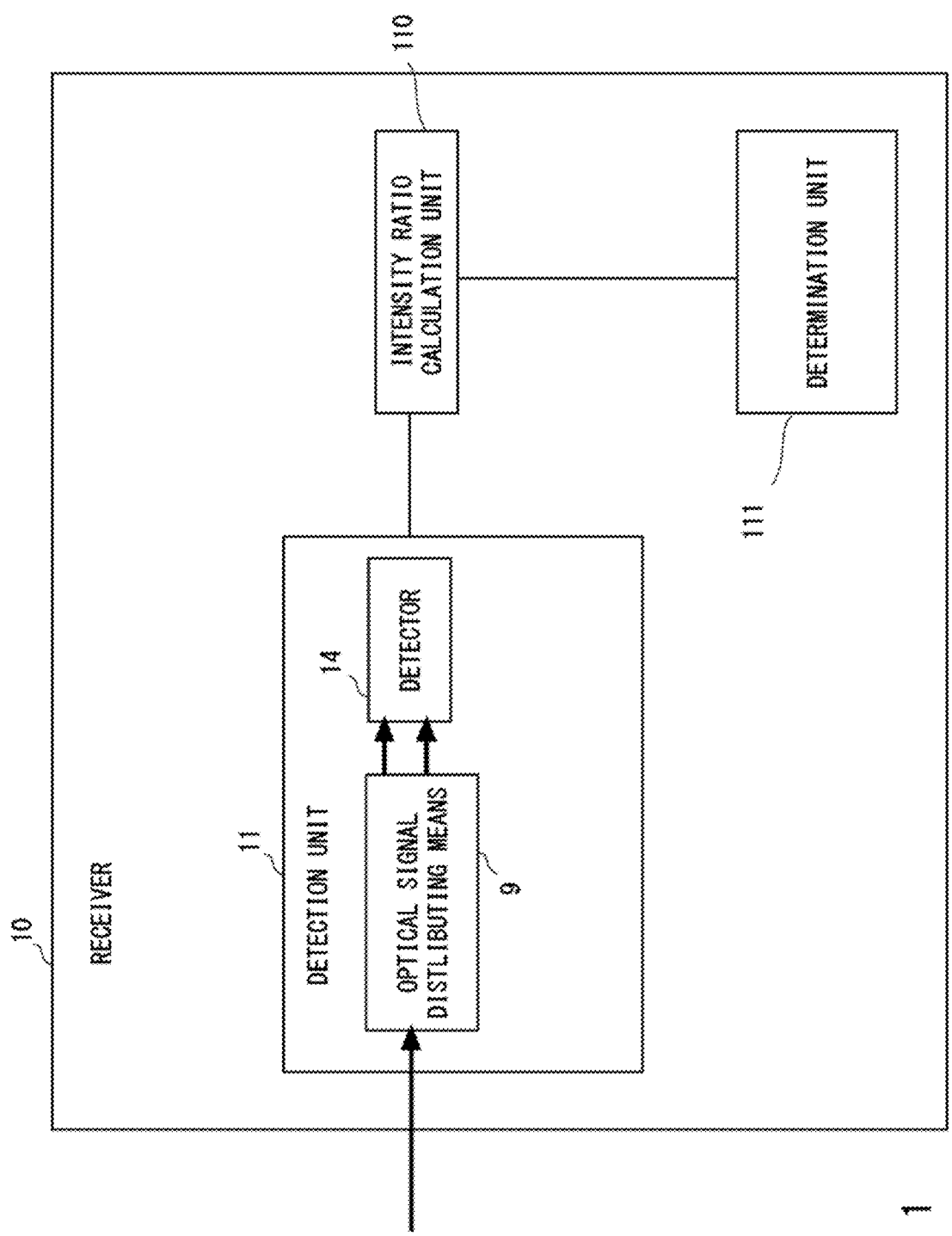
FIG. 1 is a block diagram showing a configuration of a first embodiment of the present invention.
Figure 2:
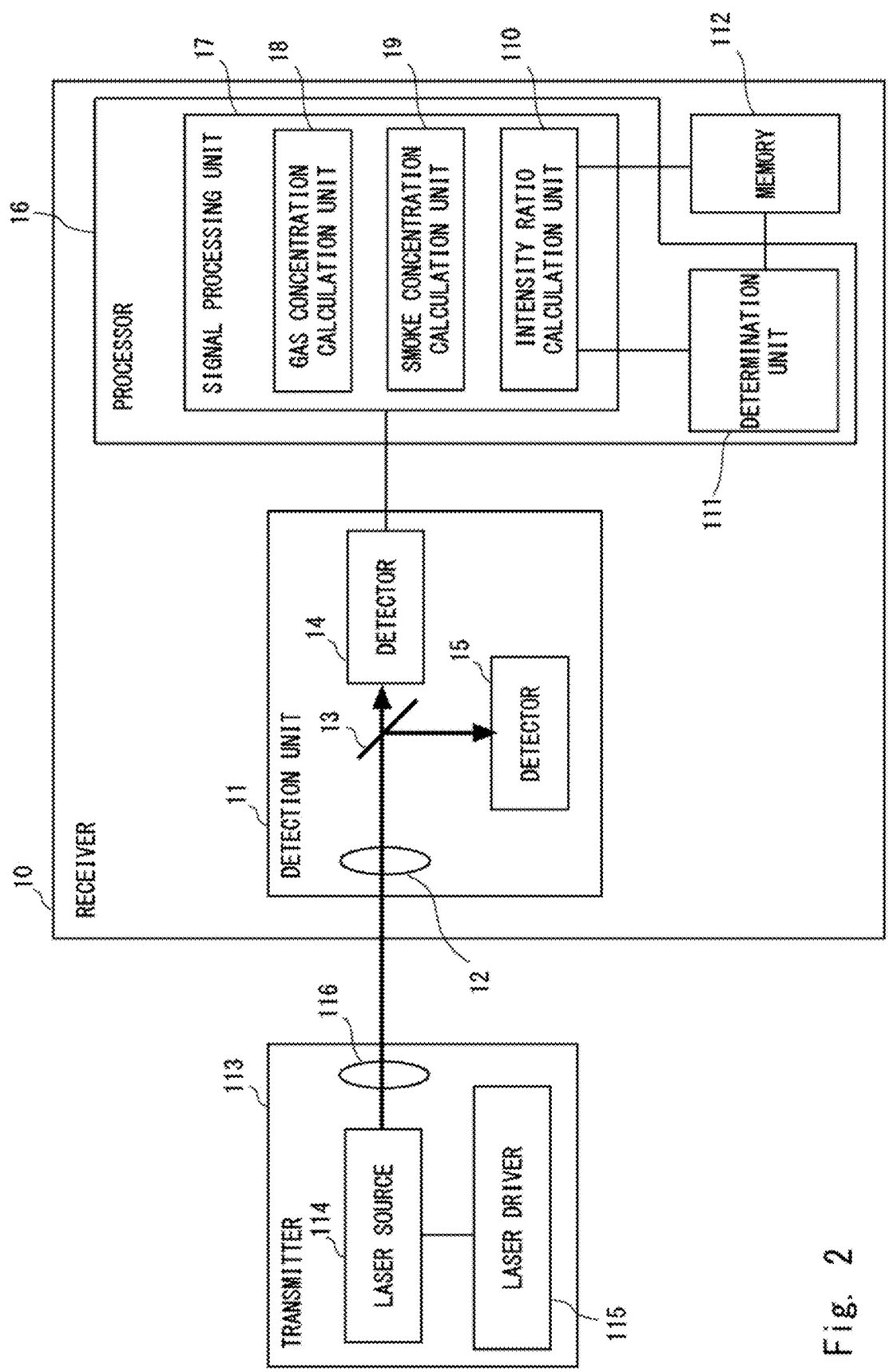
FIG. 2 is a block diagram showing a configuration of a second embodiment of the present invention.

With reference to FIG. 1, a configuration of a receiver according to an example embodiment of the present invention for detecting a detection target on a traveling path of an optical signal will be described. As shown in FIG. 1, the receiver comprises a detection unit 11, an intensity ratio calculation unit 110, and a determination unit 111. As shown in FIG. 2, a memory 112 can also be provided.

Figure 3:
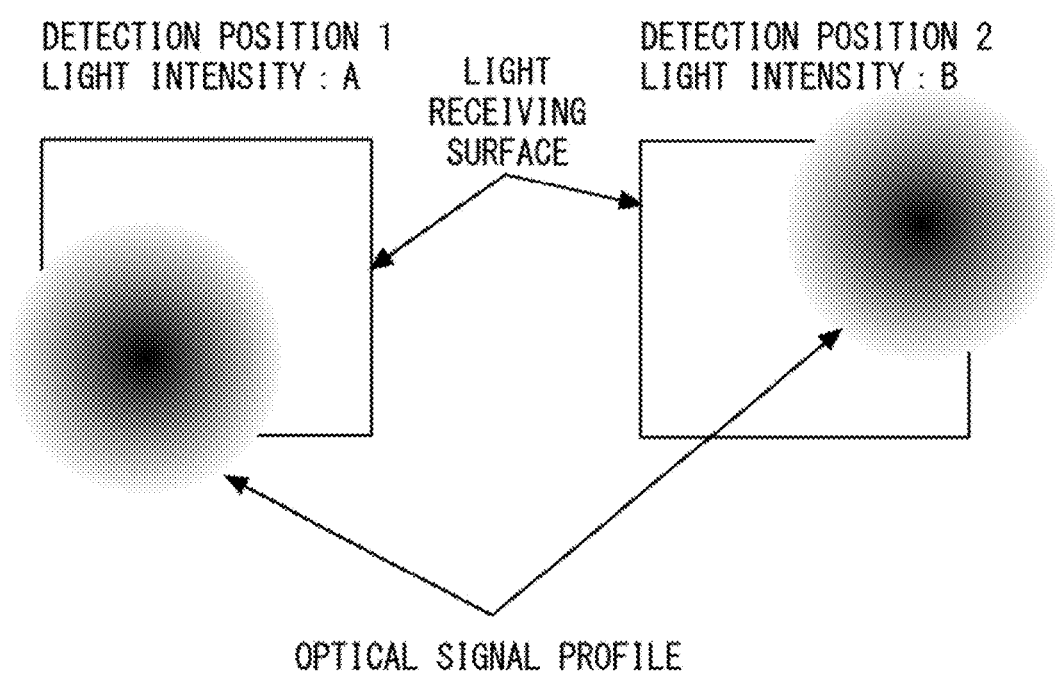
FIG. 3 is a diagram showing positions where an optical signal enters detectors according to the second embodiment.

The detection unit 11 comprises an optical signal distributing means 9 and a detector 14. As shown in FIG. 3, the detector 14 detects the amount of light received at a first position where the received light intensity increases when the optical axis of the optical signal is shifted and at a second position where the received light intensity decreases. The detector 14 outputs the detected received light intensity to the intensity ratio calculation unit 110.

The intensity ratio calculation unit 110 calculates a ratio between the received light intensity at the first position and the received light intensity at the second position. The received light intensities are outputted from the detection unit 11.

The determination unit 111 determines the presence or absence of an optical axis shift based on a change in the received light intensity ratio outputted from the intensity ratio calculation unit 110.

Figure 4:
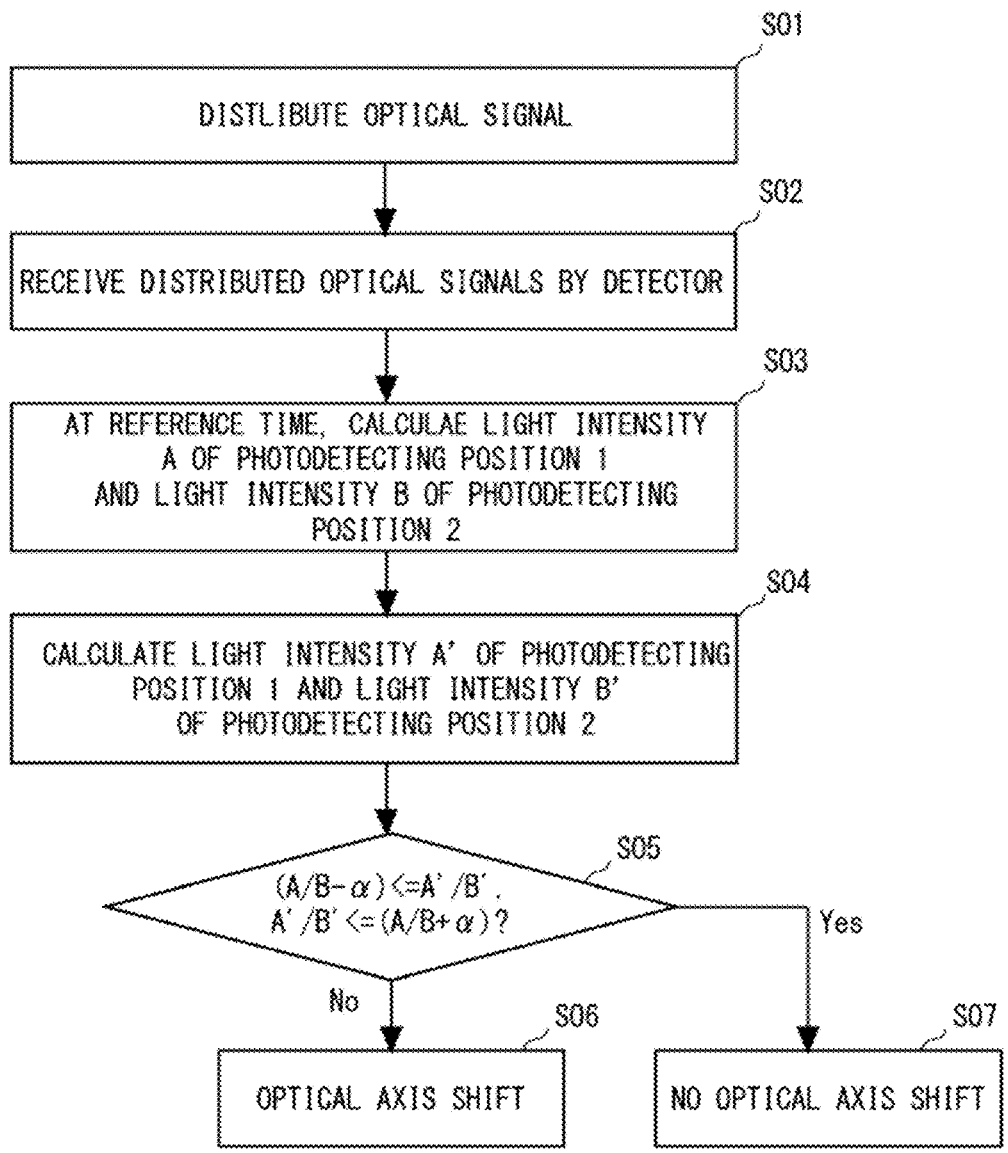
FIG. 4 is a flow chart showing the operation of the second embodiment.

Next, processing in the detection system according to the first embodiment of the present invention will be described with reference to FIG. 4.

In the detection unit 11, the optical signal distributing means 9 divides the optical signal into two or more signals (S01).

The detector 14 receives the distributed optical signals (S02).

The intensity ratio calculation unit 110 calculates the intensity ratio between signals at the two light receiving positions, wherein the signals are outputted from the detector 14 (S04).

It is necessary to calculate the initial intensity ratio between signals outputted from the detector 14 in advance and store it in the memory 112 (S03).

The determination unit 111 compares the intensity ratio calculated by the intensity ratio calculation unit 110 with the intensity ratio at the initial state stored in the memory 112 (S05). The determination unit 111 determines that there is no optical axis shift if the difference between the two intensity ratios is within a preset value $\alpha$ (S07), and determines that there is an optical axis shift if the difference is outside the range (S06). In the present embodiment, the intensity ratio in the initial state stored in the memory 112 is used as a comparison object, but the present invention is not limited thereto.

In the detection system according to the present embodiment, since the optical signal is distributed inside the receiver which is less affected by an environmental fluctuation, signal intensities received at detection positions are reduced by the same amount due to the environmental fluctuation. Therefore, by determining the intensity ratio between the signals received by the two detectors, the influence of environmental fluctuation can be eliminated. On the other hand, when the optical axis is shifted from the initial state, the intensity ratio changes because the intensity reduction amounts of the received signals at the two light receiving positions are different.

Therefore, the detection system according to the present embodiment can detect the optical axis shift even in the environment where the received light intensity fluctuates.

Second Embodiment

With reference to FIG. 2, configuration of an optical axis shift detection system according to an embodiment of the present invention will be described. As shown in FIG. 2, the detection system comprises a transmitter 113 and a receiver 10. The detection system receives an optical signal outputted from the transmitter 113 by the receiver 10. The receiver 10 detects the presence of a detection target (e.g., gas) on the traveling path between the transmitter 113 and the receiver 10 based on the reception intensity of the optical signal.

The transmitter 113 comprises a laser light source 114, a laser driver 115, and a condenser 116.

The laser driver 115 controls the temperature and the driving current of the optical signal outputted from the laser light source 114 and modulates the wavelength of the optical signal. The laser light source 114 outputs the optical signal having a time-varying wavelength in the vicinity of $\lambda 1$ μm. $\lambda 1$ is a wavelength included in an absorption band of a molecule included in a gas to be measured. An absorption band is a wavelength range in which absorption occurs when light enters a substance. The optical signal outputted from the laser light source 114 may be either a pulse light or a continuous light, and may have any cross-sectional intensity distribution.

The receiver 10 comprises a detection unit 11, a processor 16, and a memory 112.

The detection unit 11 comprises a condenser 12, a beam splitter 13, and detectors 14 and 15. The beam splitter 13 divides the optical signal into two. The detectors 14 and 15 are shifted from the position where the received light intensity becomes maximum so that the received light intensity slightly decreases. FIG. 3 shows optical signal profiles and light receiving surfaces of the detectors 14 and 15.

Note that the beam splitter 13 causes the detector 15 to reverse the shift direction of either the left/right direction or the upper/lower direction with respect to the other detector 14. Therefore, from the position shown in FIG. 3, the shift direction of the optical axis incident on detector 15 is inverted in the left/right direction if the inversion direction by the beam splitter 13 is in the left/right direction, and the shift direction is inverted in the upper/lower direction if the inversion direction is in the upper/lower direction.

The processor 16 comprises a signal processing unit 17 and a determination unit 111.

The signal processing unit 17 comprises a gas concentration calculation unit 18, a smoke concentration calculation unit 19, and an intensity ratio calculation unit 110.

The gas concentration calculation unit 18 calculates gas concentration based on an average value of electric signals outputted from one of the two detectors or from both detectors.

The smoke concentration calculation unit 19 calculates the smoke concentration based on an electric signal outputted from one of the two detectors or the average value of the electric signals outputted from both detectors.

The intensity ratio calculation unit calculates an intensity ratio between the signals outputted from the two detectors 14 and 15 in the detection unit 11.

The determination unit 111 determines the presence or absence of an optical axis shift from the received light intensity ratio outputted from the intensity ratio calculation unit 110 and the received light intensity ratio at the initial state stored in the memory 112.

The signal processing unit 17 and the determination unit 111 may be software or a module in which processing is executed by the processor 16 executing a program stored in a memory. The signal processing unit 17 and the determination unit 111 may be a circuit or hardware such as a chip.

The processor 16 reads the software (computer program) from the memory and performs the processing described later using a flowchart or the like. Processor 16 may be, for example, a microprocessor, a micro processing unit (MPU), or a central processing unit (CPU). Processor 16 may comprise a plurality of processors.

The memory 112 stores the initial ratio between the received light intensities of the detectors 14 and 15 calculated by the intensity ratio calculation unit 110.

Next, processing in the detection system according to the first embodiment of the present invention will be described with reference to FIG. 4.

In the detection unit 11, the beam splitter 13 divides the optical signal into 2 or more signals (S01).

The detectors 14 and 15 receive the optical signals divided by the beam splitter 13 (S02).

The intensity ratio calculation unit 110 calculates the intensity ratio between the signals outputted from the detectors 14 and 15 (S04).

In the initial state, it is necessary to calculate the intensity ratio between the signals outputted from the detectors 14 and 15 and store it in the memory 112 (S03).

The determination unit 111 compares the intensity ratio calculated by the intensity ratio calculation unit 110 with the initial intensity ratio stored in the memory 112 (S05).

The determination unit 111 determines that there is no optical axis shift if a difference between the two intensity ratios is within a preset value $\alpha$ (S07), and determines that there is an optical axis shift if the difference is outside the range (S06).

Figure 12:
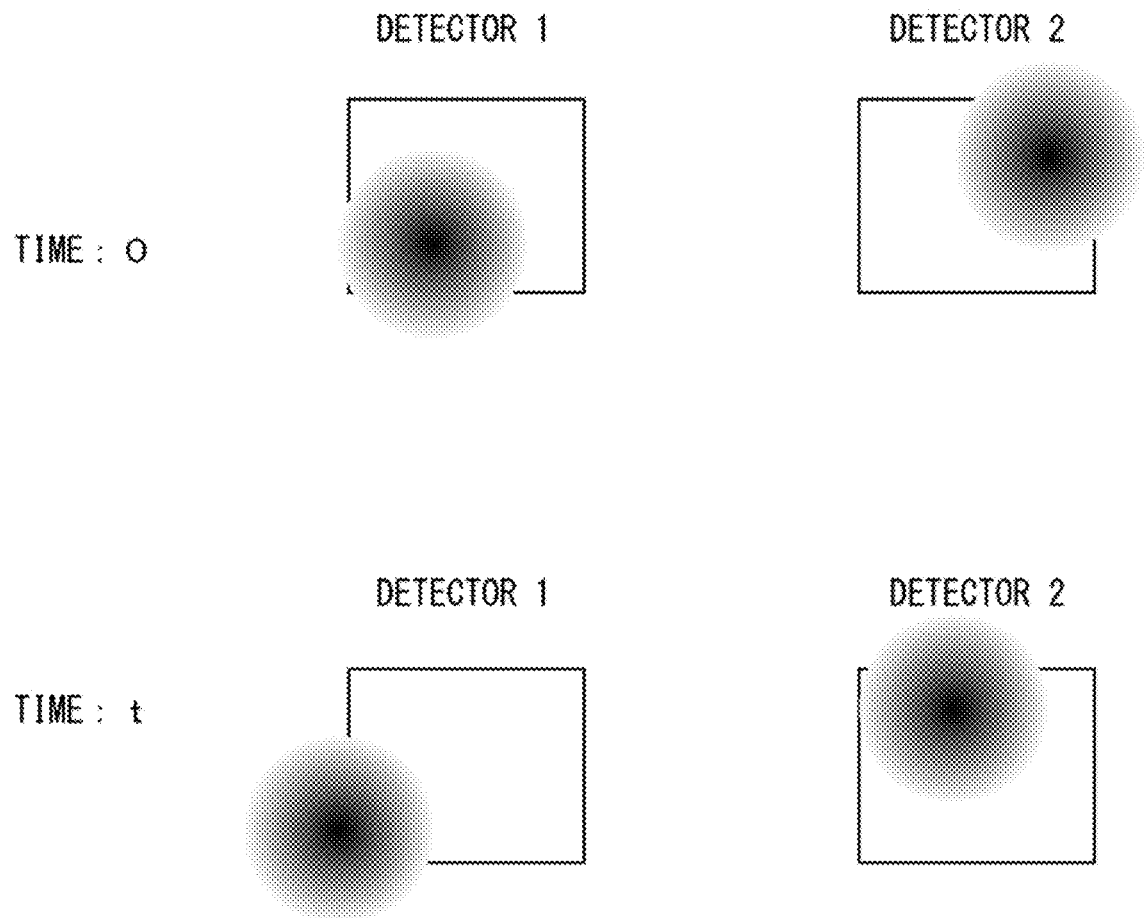
FIG. 12 is a diagram showing profiles of optical signals in an initial state and the profiles when the optical axis is shifted at time t according to the second embodiment.
Figure 13A:
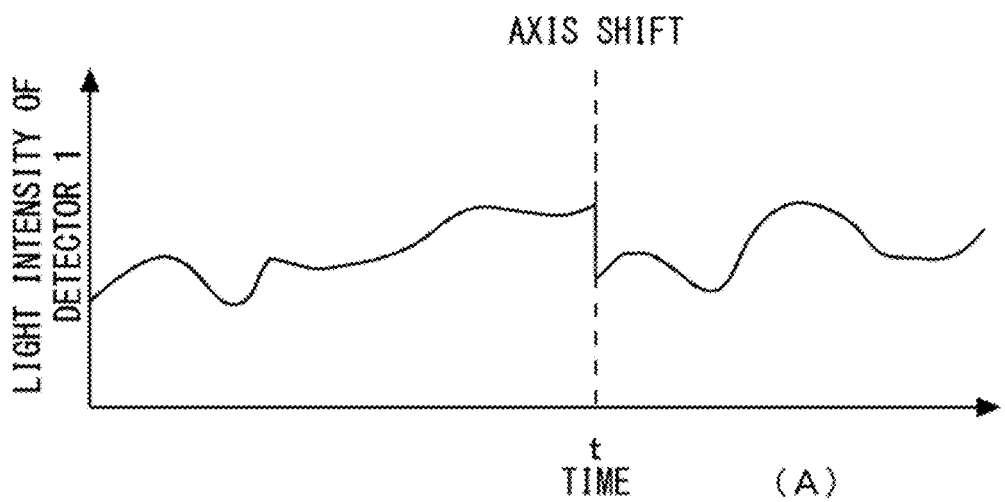
FIG. 13 A is a graph showing a change in the received light intensity of a detector 1 with time when the optical axis is shifted at time t according to the second embodiment.
Figure 13B:
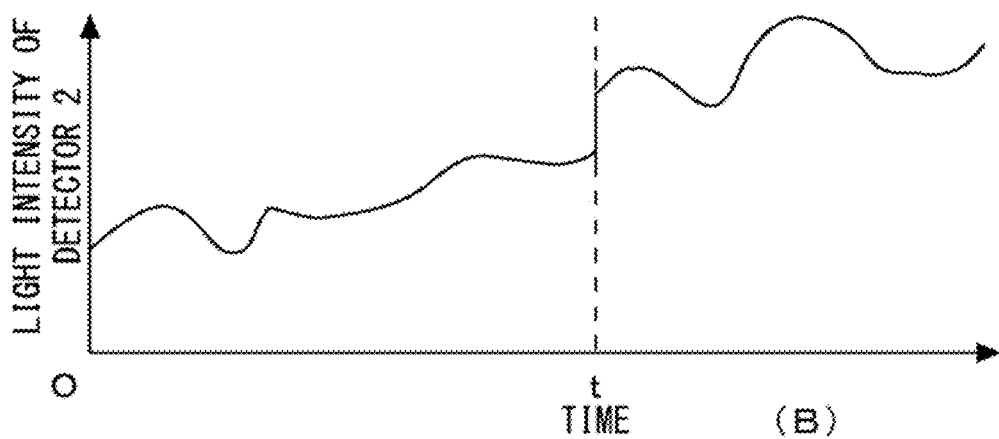

With reference to FIGS. 12, 13 A, 13 B, and 14, the operation in the case when the optical axis is shifted under the environment where the received light intensity changes will be described. Assume that the optical axis is shifted at time t as shown in FIG. 12. As shown in FIGS. 13 A and 13 B, the received light intensities of the detectors 1 and 2 similarly change before time t, and the ratio is constant as shown in FIG. 14.

At time t, when the optical axis is shifted to the left with respect to the light receiving surface as shown in FIG. 12, the received light intensity of the detector 1 decreases because the light incident on the light receiving surface decreases as shown in FIG. 12. On the other hand, the received light intensity of the detector 2 increases because the light incident on the light receiving surface increases.

Figure 14:
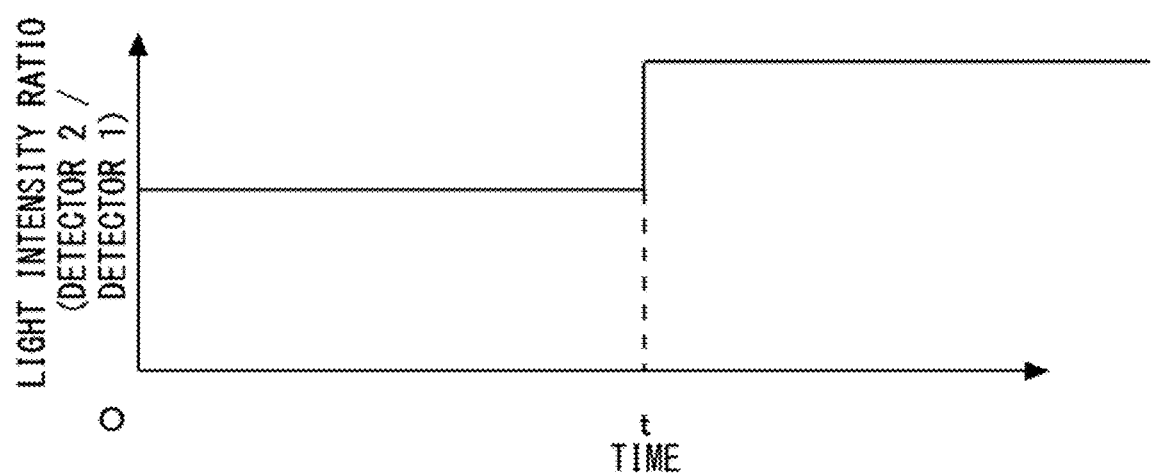
FIG. 14 is a graph showing a change in the intensity ratio between two detectors when the optical axis is shifted at time t according to the second embodiment.

Therefore, the received light intensity ratio changes at time t as shown in FIG. 14. By the change in the received light intensity ratio, the optical axis shift can be detected even under the environment where the received light intensity changes.

In the present embodiment, the signals received by the two detectors have the same intensity reduction amount due to the influence of environmental fluctuation. This is because the optical signal is emitted from one light source and is divided in the receiver which is less susceptible to environmental fluctuation.

Therefore, the influence of environmental fluctuation can be eliminated by determining the intensity ratio between the signals received by the two detectors.

When the optical axis is shifted from the initial state, the intensity ratio changes because the intensity reduction amounts of the signals received by the two detectors are different from each other. For this reason, the optical axis shift from the initial state can be detected even in the environment where the received light intensity fluctuates.

The contents of the present embodiment are not limited to the above description.

Figure 5:
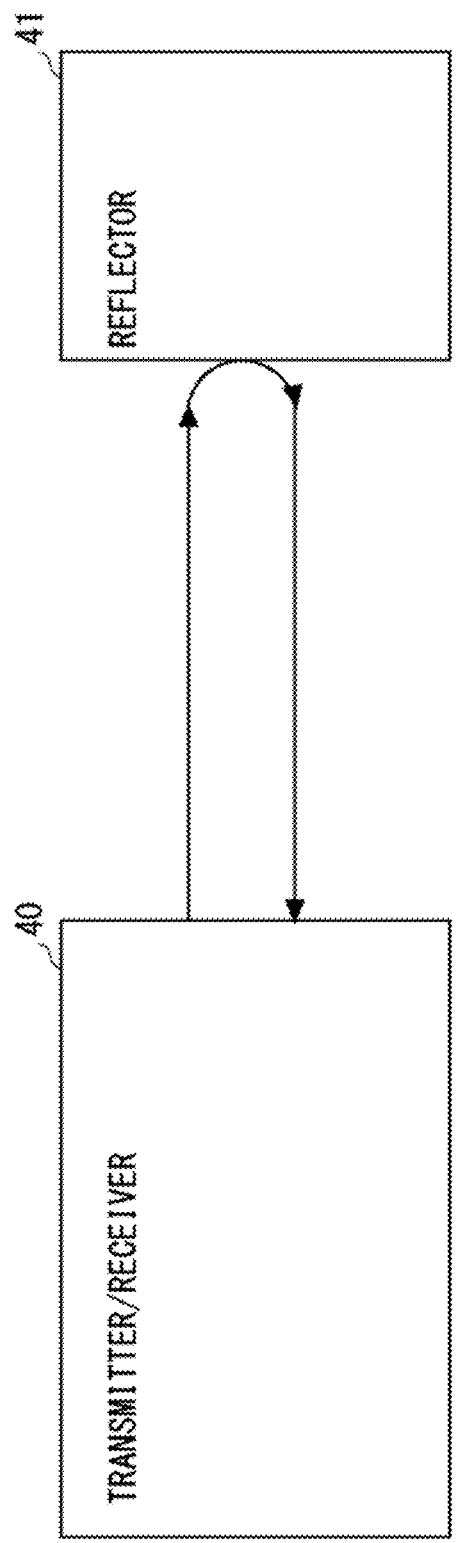
FIG. 5 is a diagram showing a transmitter/receiver integrating a transmitter and a receiver according to the second embodiment.

In the above description, the transmitter 113 and the receiver 10 are used separately, but as shown in FIG. 5, the transmitter/receiver 40 may be used. The optical signal outputted from the transmitter/receiver 40 is reflected by the reflector 41 toward the transmitter/receiver 40 and received by the transmitter/receiver 40. The reflector 41 and the transmitter-receiver 40 are arranged so as to sandwich a space to be measured. As a result, the number of devices requiring power supply can be reduced to one, and the number of devices requiring explosion-proof measures can be reduced.

Alternatively, the optical signal outputted from the transmitter/receiver 40 may be reflected a plurality of times before being received by the transmitter/receiver 40 to increase a propagation distance. Thus, the measurement accuracy can be improved.

In the above description, the optical signal is divided into two by the beam splitter 13 and received by the two detectors 14 and 15, but a movable mirror may be used instead of the beam splitter, and the position of the optical axis may be changed at a fixed minute interval to obtain the intensity ratio of the optical signal at each position. In this way, the intensity reduction of the optical signal due to the beam splitter is eliminated, and the number of detectors used can be reduced to one.

Third Embodiment

Figure 6:
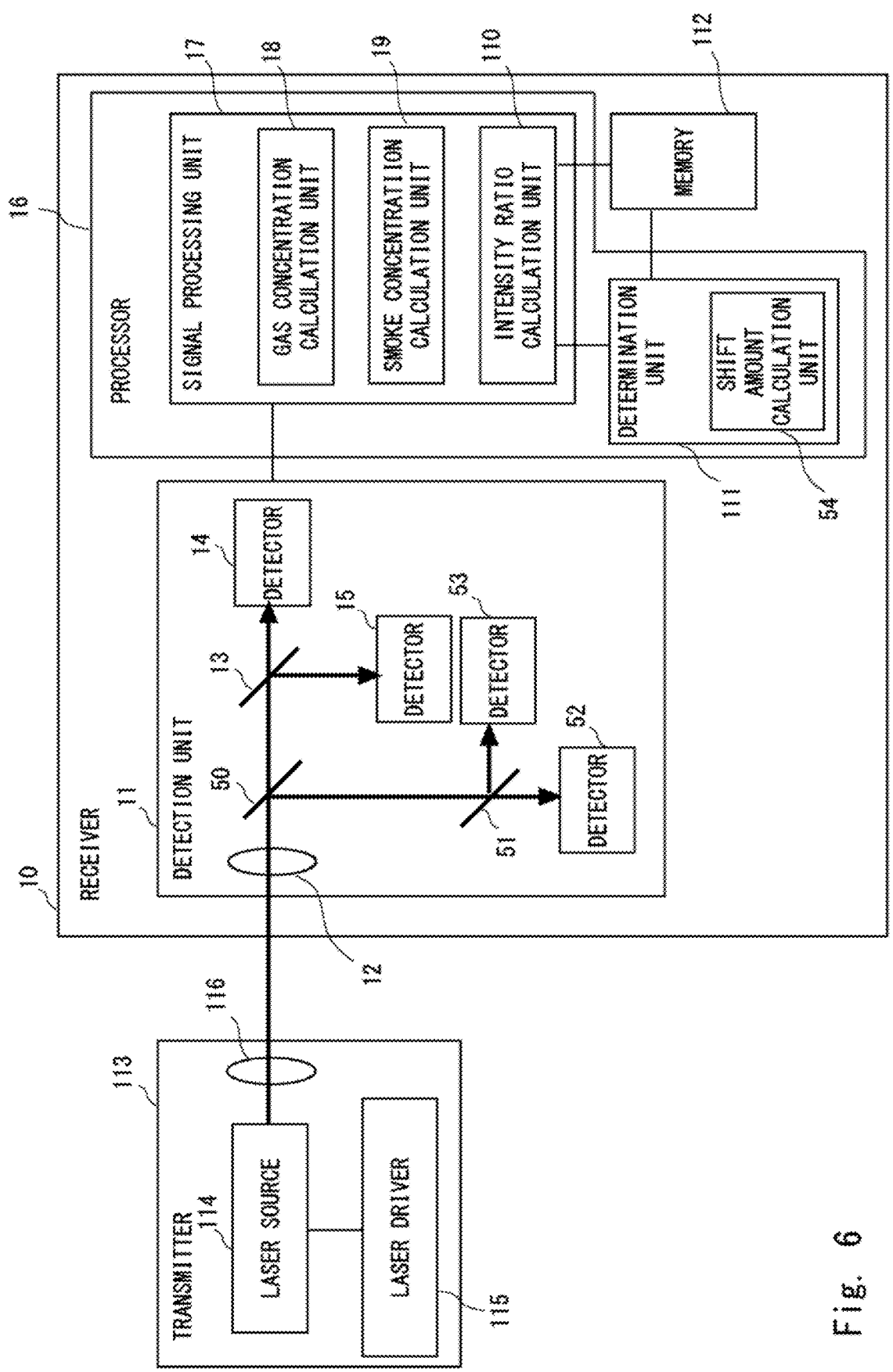
FIG. 6 is a block diagram showing a configuration of a third embodiment of the present invention.

A configuration of an optical axis shift detection system according to an embodiment of the present invention will be described with reference to FIG. 6. As shown in FIG. 6, the detection system comprises a transmitter 113 and a receiver 10.

The transmitter 113 comprises a laser light source 114, a laser driver 115, and a condenser 116.

The laser driver 115 controls the temperature and the driving current for the optical signal outputted from the laser light source 114, and modulates the wavelength of the optical signal. The laser light source 114 outputs an optical signal having a time-varying wavelength in the vicinity of $\lambda 1$ μm. $\lambda 1$ is a wavelength included in an absorption band of a molecule included in a gas to be measured. An absorption band is a wavelength range in which absorption occurs when light enters a substance. The optical signal outputted from the laser light source 114 may be either a pulse light or a continuous light, and may have any cross-sectional intensity distribution.

The receiver 10 comprises a detection unit 11, a processor 16, and a memory 112.

The detection unit 11 comprises a condenser 12, beam splitters 13, 50, 51, and detectors 14, 15, 52, 53. Beam splitters 13, 50 and 51 divide the optical signal into 4 or more.

One of the detectors 14, 15, 52 and 53 is a main detector and the other three detectors are sub-detectors. The main detector and each sub-detector may be any of the detectors 14, 15, 52 and 53.

The main detector is arranged at a position where the received light intensity is maximum.

The sub-detectors are shifted from the position where the received light intensity is maximum so that the received light intensity is slightly decreased. The three sub-detectors receive the light at any three of the following positions: a position where the received light intensity increases when the optical axis of the optical signal is shifted in the upper right direction; a position where the received light intensity increases when the optical axis is shifted in the lower right direction; a position where the received light intensity increases when the optical axis is shifted in the upper left direction; and a position where the received light intensity increases when the optical axis is shifted in the lower left direction.

Figure 7:
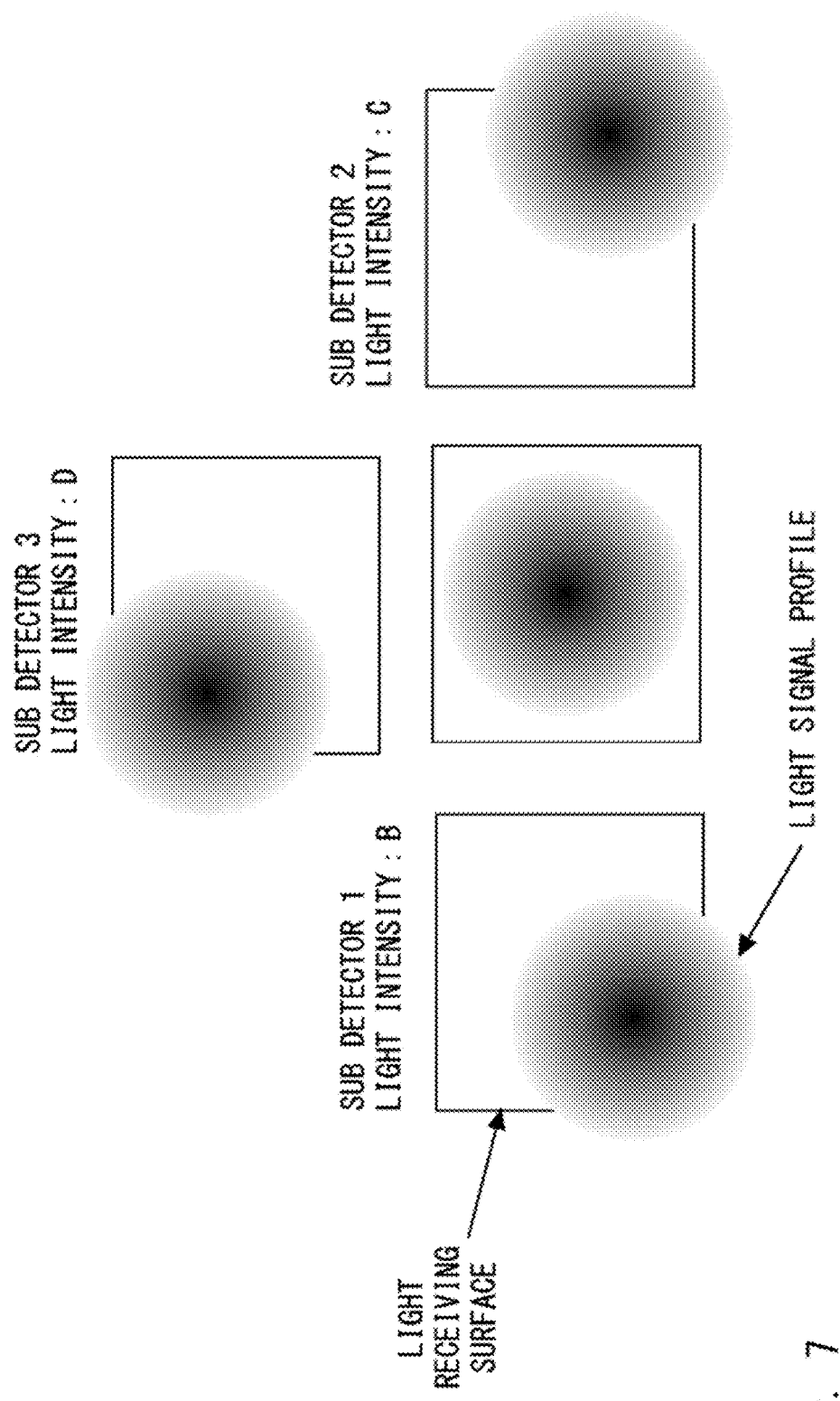
FIG. 7 shows positions where optical signals enter the detectors according to the third embodiment of the present invention.

FIG. 7 shows light receiving surfaces of the detectors 14, 15, 52 and 53 and profiles of the optical signals.

However, by the beam splitters 13 and 50, the shift directions of the detectors 15 and 52 are opposite to the shift directions of the other two detectors 14 and 53 in the left/right direction or the up/down direction. Therefore, the shift positions of the axes of the light incident on the detectors 15 and 52 are inverted from the positions shown in FIG. 7, in the left/right direction if the inversion direction by the beam splitters 13 and 50 is in the left/right direction, and in the up/down direction if the inversion direction is in the up/down direction.

The processor 16 comprises a signal processing unit 17 and a determination unit 111.

The signal processing unit 17 comprises a gas concentration calculation unit 18, a smoke concentration calculation unit 19, and an intensity ratio calculation unit 110.

The gas concentration calculation unit 18 calculates gas concentration based on an electric signal outputted by the main detector.

The smoke concentration calculation unit 19 calculates the smoke concentration based on the electric signal outputted by the main detector.

The intensity ratio calculation unit calculates the ratio between the received light intensity of the main detector and the received light intensity of each sub detector based on the intensities of signals outputted from the four detectors 14, 15, 52, and 53 of the detection unit 11.

The determination unit 111 determines the presence or absence of the optical axis shift and the direction of the optical axis shift based on the received light intensity ratio outputted from the intensity ratio calculation unit 110 and the received light intensity ratio in the initial state stored in the memory 112.

The determination unit 111 has a shift amount calculation unit 54. The shift amount calculation unit 54 calculates a shift amount of the optical axis based on the received light intensity ratio outputted from the intensity ratio calculation unit 110 and the received light intensity ratio in the initial state stored in the memory 112.

The signal processing unit 17 and the determination unit 111 may be software or a module in which processing is executed by the processor 16 executing a program stored in a memory.

The processor 16 reads the software (computer program) from the memory and performs the processing described later using a flowchart or the like. Processor 16 may be, for example, a microprocessor, a micro processing unit (MPU), or a central processing unit (CPU). Processor 16 may comprise a plurality of processors.

The memory 112 stores the initial ratio between the received light intensity of the main detector and the received light intensity of each sub detector calculated by the intensity ratio calculation unit 110.

Figure 8:
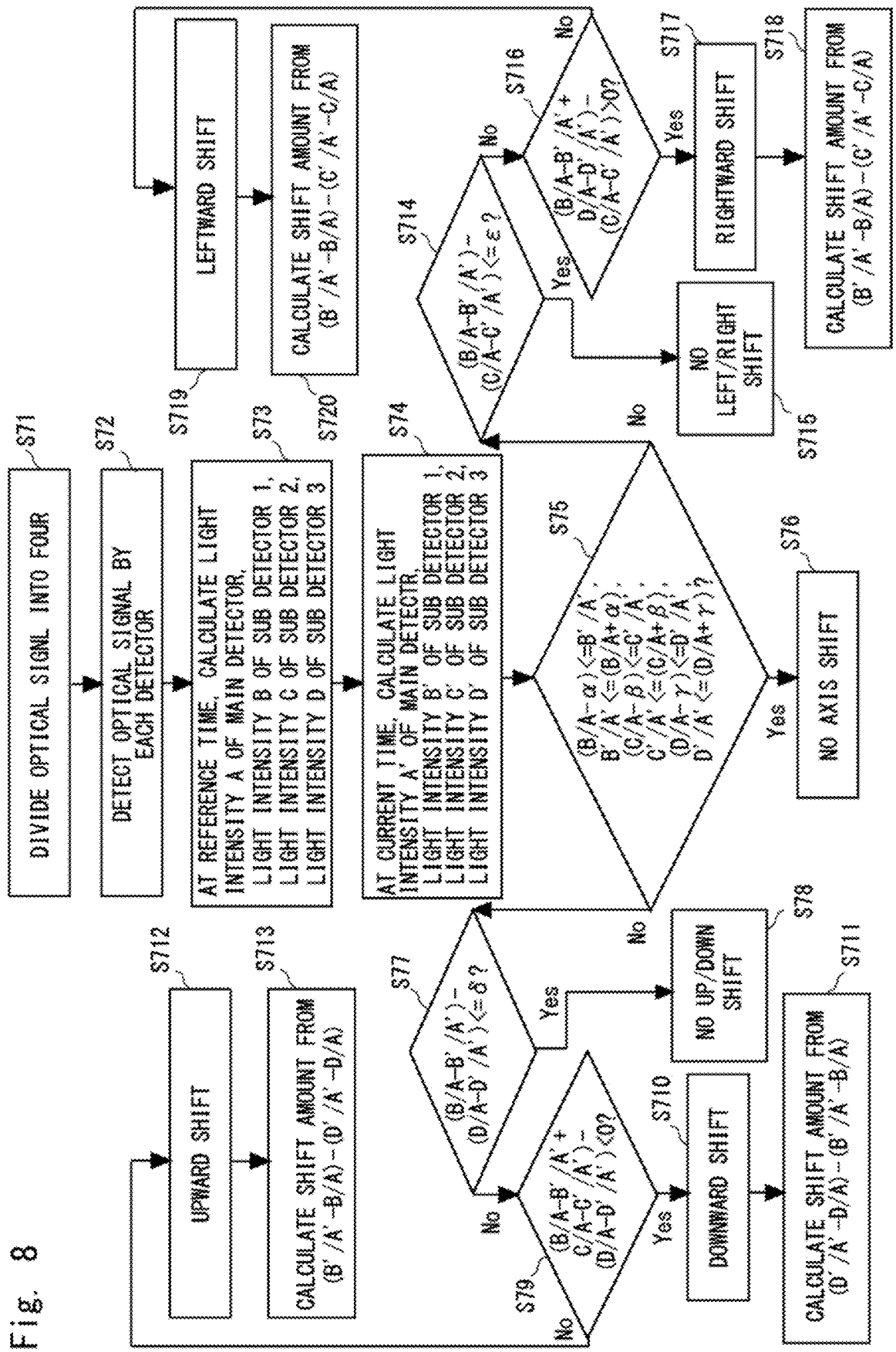
FIG. 8 is a flow chart showing the operation of the third embodiment.

Next, processing in the detection system according to the third embodiment of the present invention will be described with reference to FIG. 8.

In the detection unit 11, the beam splitters 13, 50 and 51 divide the optical signal outputted from the laser light source 114 into 4 (S 71).

In the detector 11, the four detectors 14, 15, 52, and 53 receive the optical signals divided by the beam splitters 13, 50, and 51 (S 72).

In the detection unit 11, the detectors 14, 15, 52, and 53 convert the received optical signals into electric signals and output the electric signals to the signal processing unit 17.

The intensity ratio calculation unit 110 calculates the intensity ratio between a signal outputted from the main detector and a signal outputted from each sub detector (S 74).

Here, it is necessary to calculate the initial intensity ratio between a signal outputted from the main detector and a signal outputted from each sub detector in advance, and store the intensity ratio in the memory 112 (S 73).

The determination unit 111 compares the intensity ratio calculated by the intensity ratio calculation unit 110 with the initial intensity ratio stored in the memory 112 (S 75).

The determination unit 111 determines that there is no optical axis shift if the differences between the intensity ratios are within the range of the preset values $\alpha$, $\beta$, $\gamma$ (step 76).

When it is determined that there is an optical axis shift, if the difference between the intensity ratio of the sub-detector 1 to the main detector and that of the sub-detector 3 to the main detector is not more than a preset value $\delta$ (S 77), it is determined that there is no optical axis shift in the up/down direction (S 78).

Similarly, if the difference between the intensity ratio of the sub-detector 1 to the main detector and that of the sub-detector 2 to the main detector is not more than a preset value $\varepsilon$ (S 714), it is determined that there is no optical axis shift in the left/right direction (S 715).

When it is determined that there is an optical axis shift in the up/down direction, it is determined which is larger: the sum of the change amount of the intensity ratio of each detector where the optical axis is shifted downward from the center to the main detector; or the sum of the change amount of the intensity ratio of each detector where the optical axis is shifted upward from the center to the main detector (S 79).

In step 79, when the sum of the change amount of the intensity ratio of each detector shifted upward to the main detector is larger, it is determined that there is a downward shift (step 710), and the shift amount is calculated (step 711).

In step 79, when the sum of the change amount of the intensity ratio of each detector shifted upward to the main detector is smaller, it is determined that there is an upward shift (step 712), and the shift amount is calculated (step 713).

When it is determined that there is an optical axis shift in the left/right direction, it is determined which is larger: the sum of the change amount of intensity ratio of each detector where the optical axis is shifted in the left direction from the center to the main detector; or the sum of the change amount of the intensity ratio of each detector where the optical axis is shifted in the right direction from the center to the main detector (S 716).

In step 716, when the sum of the change amount of the intensity ratio of each detector shifted in the left direction to the main detector is larger, it is determined that there is a shift in the right direction (step 717), and the shift amount is calculated by the shift amount calculation unit 54 (step 718).

In step 716, when the sum of the change amount of the intensity ratio of each detector shifted in the left direction to the main detector is smaller, it is determined that there is a shift in the left direction (step 719), and the shift amount is calculated by the shift amount calculation unit 54 (step 720).

Figure 15:
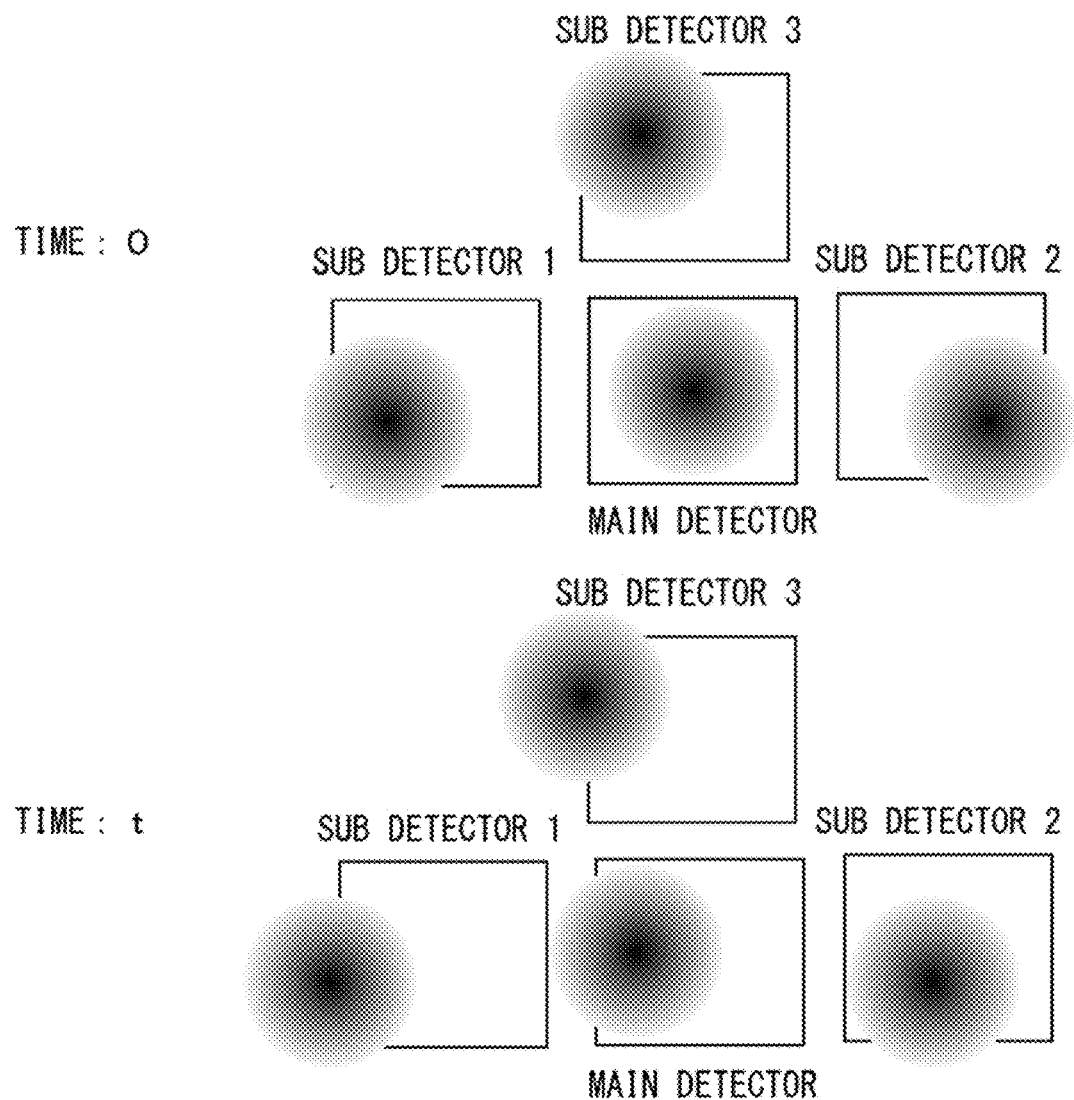
FIG. 15 is a diagram showing profiles of optical signals in an initial state and profiles when the optical axis is shifted at time t according to the third embodiment.
Figure 16A:
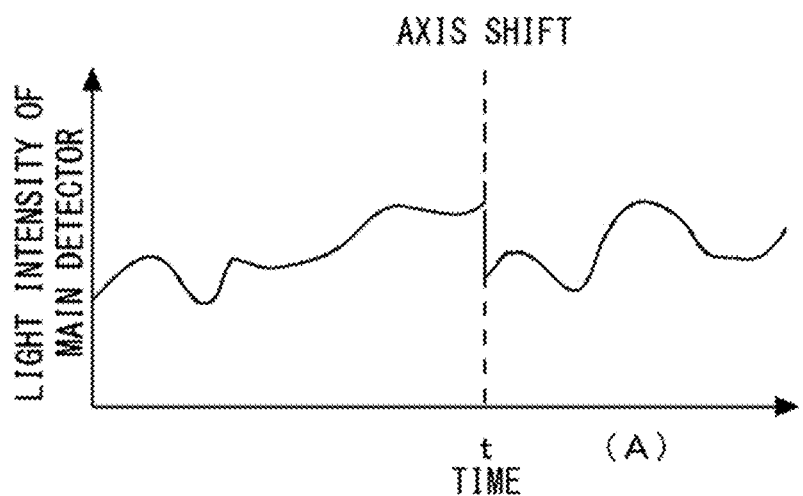
FIG. 16 A is a graph showing a change in the received light intensity of a main detector when the optical axis is shifted at time t according to the third embodiment.
Figure 16B:
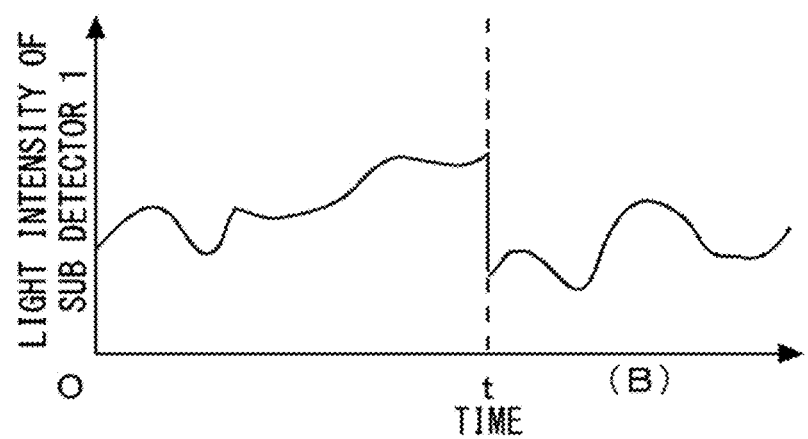
Figure 16C:
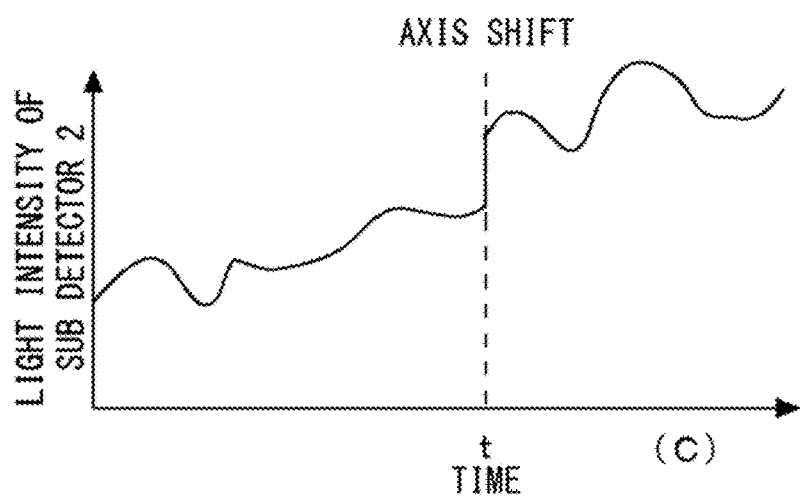
Figure 16D:
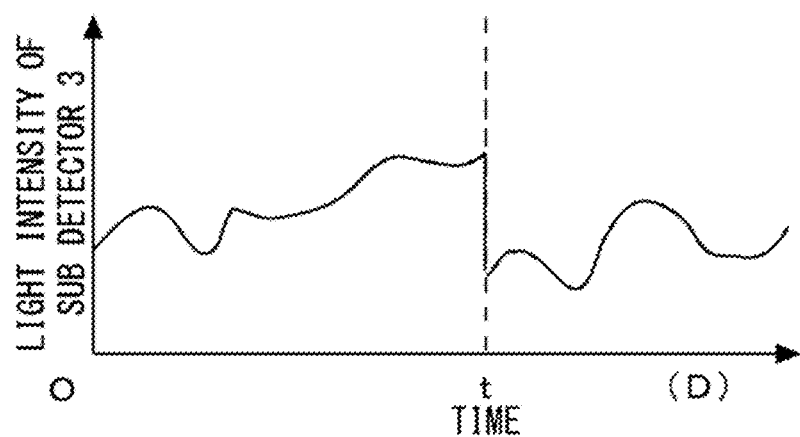
Figure 17A:
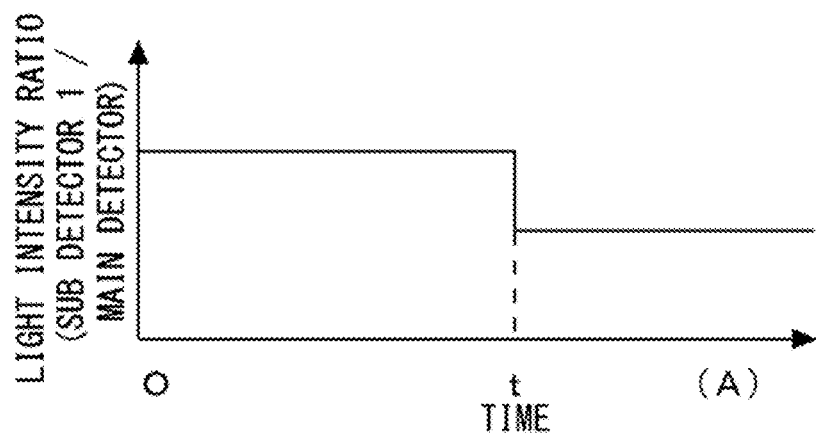
FIG. 17 A is a graph showing a change in the received light intensity ratio between the sub-detector 1 and the main detector when the optical axis is shifted at time t according to the third embodiment.
Figure 17B:
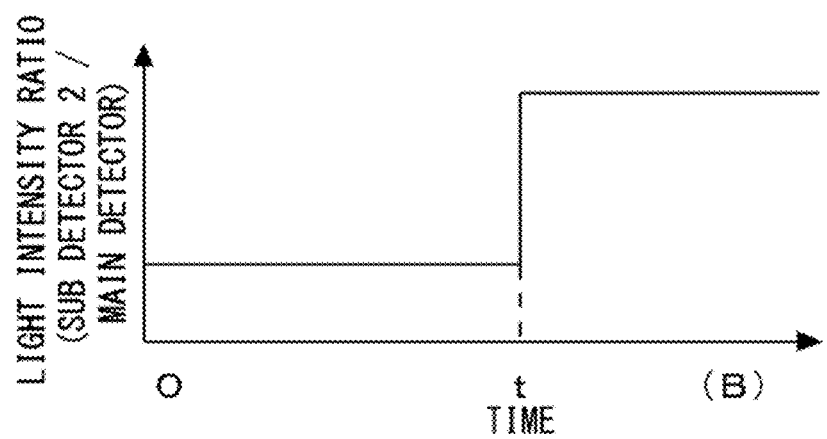
Figure 17C:
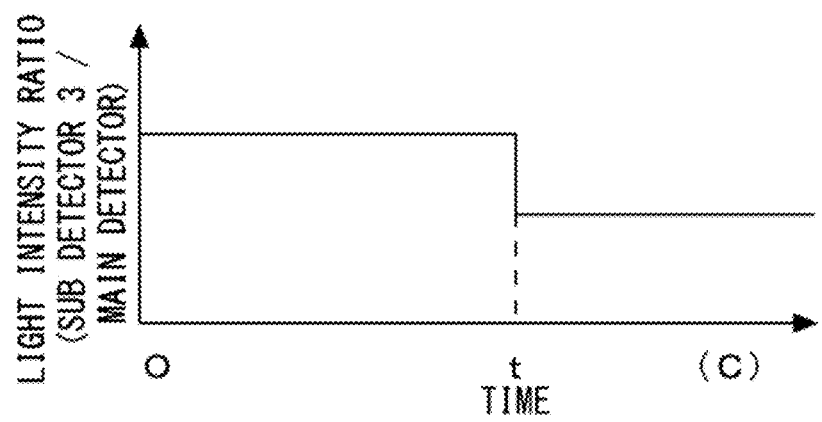
Figure 18A:
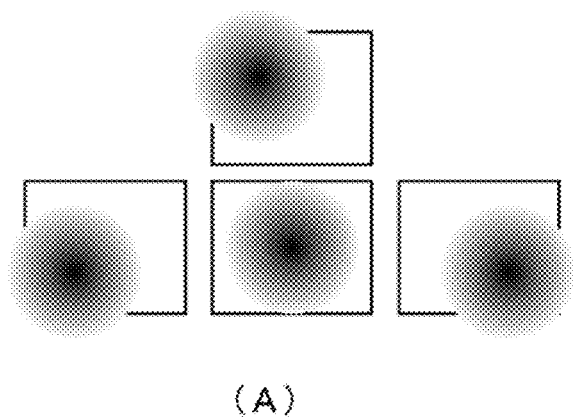
FIG. 18 A shows the initial optical axis positions (A) of optical signals incident on the light receiver according to the third embodiment.
Figure 18B:
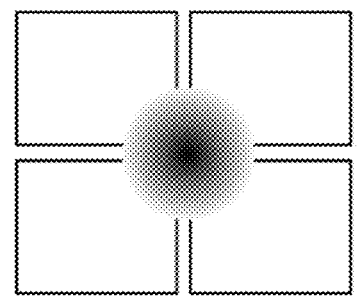
Figure 18C:
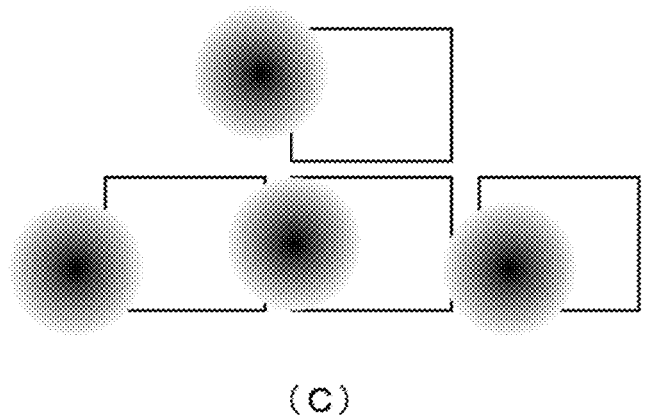
Figure 18D:
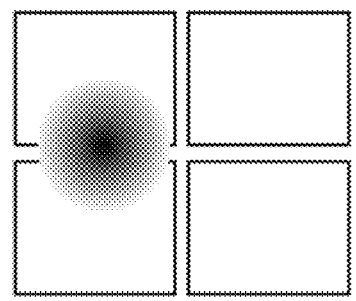

With reference to FIGS. 15, 16 A, 16 B, 16 C, 16 D, 17 A, 17 B, and 17 C, an operation when the optical axis shift occurs under an environment where the received light intensity changes will be described. Assume that an optical axis shift occurs at time t as shown in FIG. 15. As shown in FIGS. 16 A, 16 B, 16 C, and 16 D, the received light intensities of the four detectors similarly change before time t, and the ratios are constant as shown in FIGS. 17 A, 17 B, and 17 C.

At time t, since the optical axis shifts to the left with respect to the light receiving surface as shown in FIG. 15, the light incident on the light receiving surface of the main detector is slightly reduced as shown in FIG. 15, so that the received light intensity is also slightly reduced. In the sub-detector 1, the light incident on the light receiving surface is greatly reduced, so that the received light intensity is also greatly reduced. In the sub-detector 2, the received light intensity increases because the light incident on the light receiving surface increases. In the sub-detector 3, the light incident on the light receiving surface is greatly reduced, so that the received light intensity is also greatly reduced. Therefore, at time t, the received light intensity ratios change as shown in FIGS. 17 A, 17 B, and 17 C. By capturing the change in the received light intensity, the optical axis shift can be detected even in the environment in which the received light intensity changes due to gas, smoke, dust, or the like, and the shift direction and the shift amount can be calculated.

In this embodiment, the signals received by the four detectors have the same amount of intensity change due to the influence of environmental fluctuation. Therefore, the influence of environmental fluctuation can be eliminated by determining the intensity ratio between the signals received by the four detectors.

When the optical axis is shifted from the initial state, the intensity ratio changes because the change amount of the signal intensity received by each of the four detectors is different. When the light incident on the three sub-detectors is shifted in one direction, the received light intensity of one or more of the three detectors is increased, and the received light intensity of the other detectors is decreased. Therefore, whether the received light intensity is increased or decreased depends on the shift direction. For these reasons, the optical axis shift from the initial state can be detected and the shift direction and the shift amount can be calculated even in an environment where the received light intensity fluctuates.

Further, in the present embodiment, it is possible to detect larger optical axis shifts compared with a general capture and tracking technique used in an optical space communication system.

Figure 10:
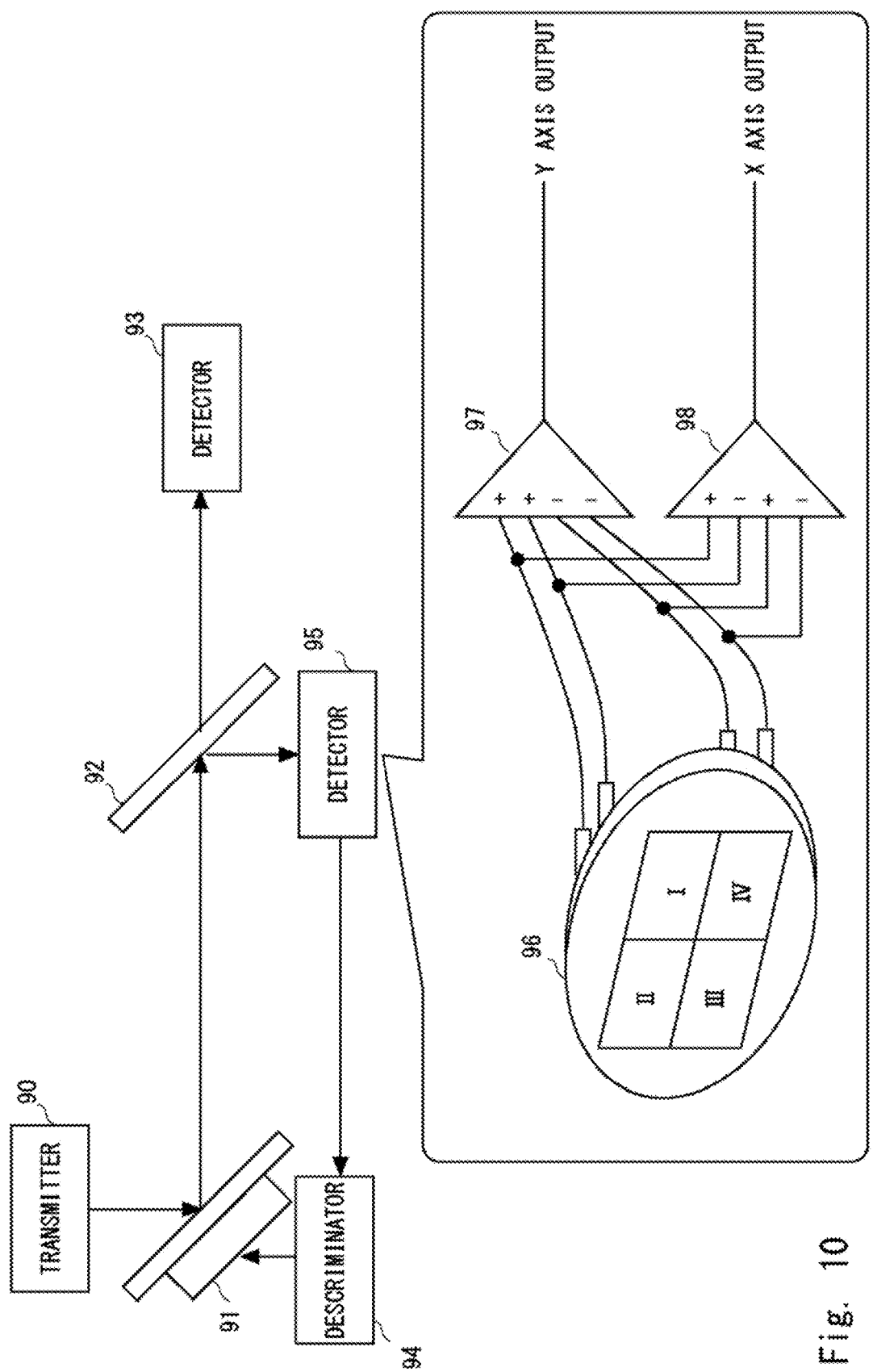
FIG. 10 is a conceptual diagram of a general capture and tracking technique used in optical communication systems.
Figure 11A:
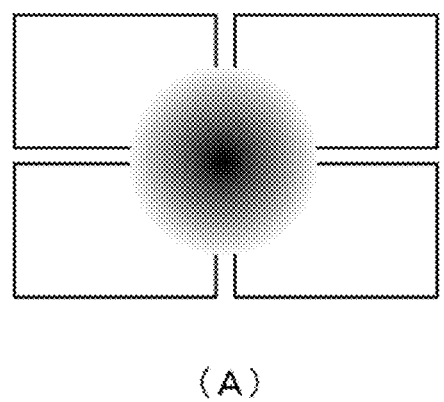
FIG. 11 A shows a light receiving surface and an optical signal profile when there is no optical axis shift in the general capture and tracking technique used in optical communication systems.
Figure 11B:
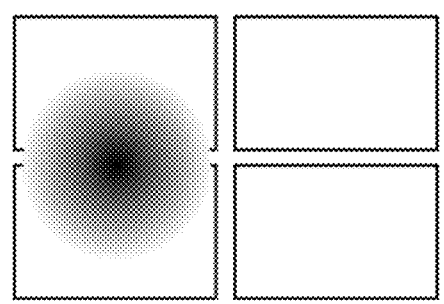

FIG. 10 is a conceptual diagram of the general capture and tracking technique. A detector 95 receives the optical signal divided by the beam splitter 92. The detector 95 detects the variation of the received light focal position as the optical axis shift amount by using a quad photodetector 96 and amplifiers 97, 98. The optical axis shift can be detected based on the received light intensities of the four detectors of the quad photodetector 96. In this case, if received light amounts become 0 as shown in FIG. 18 D, the amounts do not change even if the optical axis is shifted further, and the optical axis shift amount cannot be obtained.

FIGS. 18 A, 18 B, 18 C, and 18 D show examples of light receiving surfaces and profiles of optical signals, (A) and (C) show an initial state and a state when there is an optical axis shift in this embodiment, and (B) and (D) show an initial state and a state when there is an optical axis shift in the general capture and tracking technique used in an optical space communication system. FIG. 18 C shows optical axis positions of the optical signal incident on the photodetectors in this embodiment when the optical axis is shifted by the same amount as that in FIG. 18 D. In the present embodiment, since each focusing position is set to a position closer to the center, it is possible to obtain an optical axis shift amount larger than that of the general capture and tracking technique shown in FIG. 10.

The contents of the present embodiment are not limited to the above description. In the above description, the transmitter 113 and the receiver 10 are used separately, but as shown in FIG. 5, the transmitter/receiver 40 may be used. The optical signal outputted from the transmitter/receiver 40 is reflected by the reflector 41 in the direction of the transmitter/receiver 40 and received by the transmitter/receiver 40. In this way, the number of devices that require power supply can be reduced to one, and the number of devices that require explosion-proof measures can be reduced.

The optical signal outputted from the transmitter/receiver 40 may be reflected multiple times before being received by the transmitter/receiver 40 to increase the propagation distance. Thus, the measurement accuracy can be improved.

Figure 9:
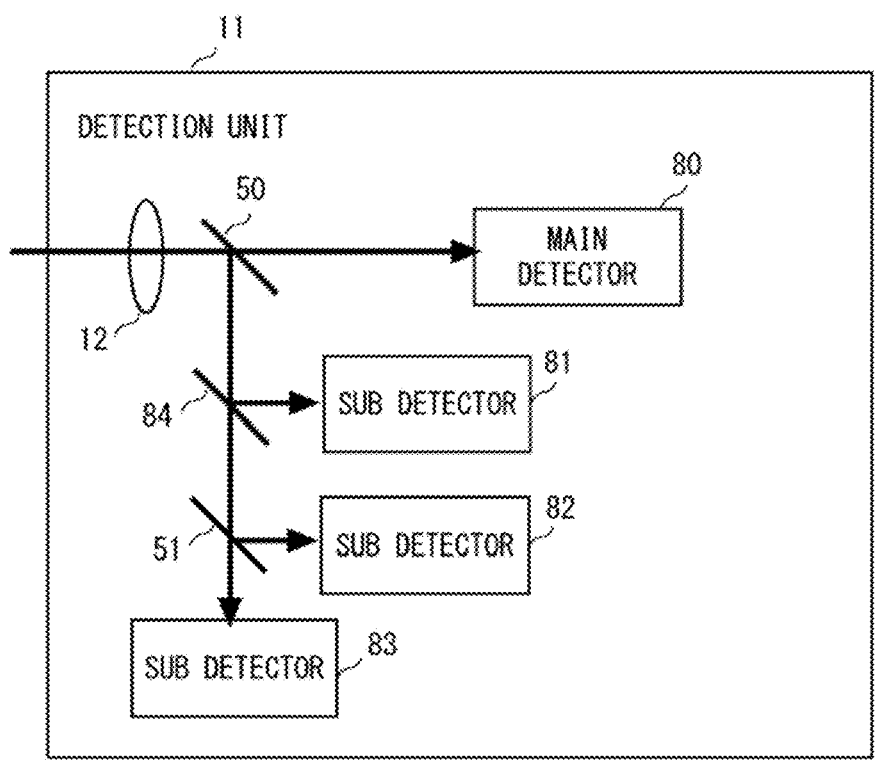
FIG. 9 shows a detection unit where the positions of beam splitters and detectors are changed according to the third embodiment.

In the above description, each of the optical signals divided into 4 passes through any of the 3 beam splitters 13, 50 and 51 twice, but the beam splitters 50, 51 and 84, the main detector 80, and the sub-detectors 81, 82 and 83 may be arranged as shown in FIG. 9. In this way, the decrease in the optical signal intensity of the main detector, which calculates the gas and smoke concentration, due to the beam splitter can be reduced.

In the above description, the optical signal is divided into 4 by the beam splitters 13, 50, and 51 and received by the 4 detectors 14, 15, 52, and 53, but a movable mirror may be used instead of the beam splitters, and the position of the optical axis may be changed at a fixed minute interval to obtain the intensity ratio between the optical signals at each position. In this way, the intensity reduction of the optical signal due to the beam splitters is eliminated, and the number of detectors used can be reduced to one.

In the above description, although an example of calculating the gas or smoke concentration from the optical signal received by the main detector is shown, the measured value may be derived by calculating the gas or smoke concentration from the optical signal received by any of the sub-detectors, or by calculating the gas or smoke concentrations from the optical signals received by some detectors or all the detectors and taking the average or median value thereof.

In the above description, optical axis positions of the detectors 15 and 52 are changed from the positions in FIG. 7, but the optical axis positions may be set to the positions in FIG. 7 and the shift directions may be corrected to be equal to the shift directions of the other detectors 14 and 53 by using a mirror.

In the above description, the present invention has been shown as an example of the wide area sensor for transmitting the optical signal and monitoring an abnormal state, but it may be used in other fields such as optical communication.

It should be noted that the present invention is not limited to the embodiment described above, and may be appropriately modified without departing from the spirit of the present disclosure.

Although the present invention has been described with reference to the embodiments, the present invention is not limited to the above. The structure and details of the present invention may be modified in various ways that would be understood by those skilled in the art within the scope of the disclosure.

This application is based upon and claims the benefit of priority from Japanese patent application No. 2019-058455, filed on Mar. 26, 2019, the disclosure of which is incorporated herein in its entirety by reference.

Some or all of the above embodiments may also be described as follows, but are not limited to the following.
(Supplementary Note 1)
  A receiver comprising:
    optical signal distributing means for distributing an optical signal transmitted for detecting a detection target on a traveling path to two or more paths;
    detection means for detecting a received light intensity of the optical signal at a first position where the received light intensity increases when the optical axis of the optical signal is shifted and at a second position where the received light intensity decreases when the optical axis is shifted;

intensity ratio calculation means for calculating a ratio between the received light intensity at the first position and the received light intensity at the second position based on the output of the detection means;

determination means for determining the presence or absence of an optical axis shift based on a change in the received light intensity ratio calculated by the intensity ratio calculation means.

(Supplementary Note 2)

A receiver comprising:

optical signal distributing means for distributing an optical signal transmitted for detecting a detection target on a traveling path to four or more paths;

detection means for detecting the received light intensity of the optical signal at a first position where the received light intensity becomes maximum, and at more than three positions out of a second position where the received light intensity increases when the optical axis of the optical signal is shifted in the upper right direction, a third position where the received light intensity increases when the optical axis of the optical signal is shifted in the lower right direction, a fourth position where the received light intensity increases when the optical axis is shifted in the upper left direction, and a fifth position where the received light intensity increases when the optical axis is shifted in the lower left direction;

determination means for determining the presence or absence of an optical axis shift and calculating the amount of the optical axis shift based on a change in the ratio between the received light intensities detected by the detection means.

(Supplementary Note 3)

The receiver according to Supplementary Note 1 or 2, wherein the determination means determine the presence or absence of the optical axis shift by comparing the ratio between the received light intensities detected by the detection means with a predetermined ratio between the initial light intensities.

(Supplementary Note 4)

The receiver according to any one of Supplementary Note 1 to 3, wherein the optical signal distributing means comprises a beam splitter.

(Supplementary Note 5)

The receiver according to any one of Supplementary Note 1 to 3, wherein the optical signal distributing means comprises a movable mirror.

(Supplementary Note 6)

A detection system comprising:

the receiver according to any one of Supplementary Note 1 to 5; and a transmitter for transmitting the optical signal, wherein the detection system detects the detection target on the traveling path of the optical signal transmitted from the transmitter.

(Supplementary Note 7)

The detection system according to Supplementary Note 6, the transmitter transmits the optical signal of a wavelength included in an absorption band of gas to be measured.

(Supplementary Note 8)

The detection system according to Supplementary Note 6 or 7, comprising:

a transmitter/receiver in which the transmitter and the receiver are integrated;

a reflector for reflecting the optical signal outputted from the transmitter/receiver to the transmitter/receiver, wherein the reflector and the transmitter/receiver are arranged so as to sandwich a space to be measured.

(Supplementary Note 9)

A detection method comprising:

distributing an optical signal in two or more paths;

receiving the distributed optical signals at a first position where the received light intensity increases when the optical axis of the optical signal is shifted and at a second position where the received light intensity decreases when the optical axis is shifted;

calculating a received light intensity ratio based on the signal intensity at the first position and the signal intensity at the second position;

determining the presence or absence of an optical axis shift based on a change in the received light intensity ratio.

(Supplementary Note 10)

A detection method comprising:

distributing an optical signal to four or more paths, detecting the distributed optical signals at a position where the received light intensity is maximum, and at more than three positions out of a position where the received light intensity increases when the optical axis of the optical signal is shifted in the upper right direction, a position where the received light intensity increases when the optical axis is shifted in the lower right direction, a position where the received light intensity increases when the optical axis is shifted in the upper left direction, and a position where the received light intensity increases when the optical axis is shifted in the lower left direction;

calculating the ratio between the received light intensity at the position where the received light intensity is maximum and each received light intensity at the three or more positions;

determining whether or not there is an optical axis shift based on whether or not a difference between each received light intensity ratio and each initial light intensity ratio is within a predetermined range;

determining whether there is a up/down shift or a left/right shift based on the difference between the amount of change of each received light intensity ratio from an initial state;

determining an optical axis shift direction based on addition and subtraction of the change amounts of respective received light intensity ratios from the initial state;

calculating a shift amount from the difference between the amount of change of each light intensity ratio from the initial state.

(Supplementary Note 11)

The method according to Supplementary Note 9 or 10, the optical signal is distributed using a beam splitter.

(Supplementary Note 12)

The method according to Supplementary Note 9 or 10, wherein the optical signal is distributed using a movable mirror.

REFERENCE SIGNS LIST

9 OPTICAL SIGNAL DISTRIBUTING MEANS
10 RECEIVER
11 DETECTION UNIT
12, 116 CONDENSER 13, 50, 51, 84, 92 BEAM SPLITTER
14, 15, 52, 53, 93, 95 DETECTOR
16 PROCESSOR
17 SIGNAL PROCESSING UNIT
18 GAS CONCENTRATION CALCULATION UNIT
19 SMOKE CONCENTRATION CALCULATION UNIT
110 STRENGTH RATIO CALCULATION UNIT
111 DETERMINATION UNIT
112 MEMORY
113, 90 TRANSMITTER
114 LASER LIGHT SOURCE
115 LASER DRIVER
40 TRANSMITTER/RECEIVER
41 REFLECTOR
54 SHIFT AMOUNT CALCULATION UNIT
80 MAIN DETECTOR
81, 82, 83 SUB-DETECTOR
91 MIRROR
94 IDENTIFIER
96 4 QUAD PHOTODETECTOR
97, 98 AMPLIFIER

What is claimed is:

1. A receiver comprising:
a divider configured to divide an optical signal transmitted for detecting a detection target on a traveling path over a plurality of paths including a first path and a second path;
a detector configured to detect a received light intensity of the optical signal at a first position of the first path where the received light intensity increases when an optical axis of the optical signal is shifted and at a second position of the second path where the received light intensity decreases when the optical axis is shifted;
a processor; and
a memory storing instructions executable by the processor to:
calculate a received light intensity ratio between the received light intensity at the first position as has been detected and the received light intensity at the second position as has been detected; and
determine presence or absence of an optical axis shift based on a change in the received light intensity ratio over time.

2. The receiver according to claim 1, wherein the presence or absence of the optical axis shift is determined by comparing the received light intensity ratio with a predetermined received light intensity ratio.

3. The receiver according to claim 1, wherein the distributor is a beam splitter.

4. The receiver according to claim 1, wherein the distributor is a movable mirror.

5. A detection system comprising:
the receiver according to claim 1; and
a transmitter for transmitting the optical signal, wherein the detection system detects the detection target on the traveling path of the optical signal transmitted from the transmitter.

6. The detection system according to claim 5,
wherein the transmitter transmits the optical signal at a wavelength included in an absorption band of gas that is measured.

7. The detection system according to claim 5,
wherein the transmitter and the receiver are integrated within a transmitter/receiver, and
the detection system further comprises a reflector for reflecting the optical signal outputted from the transmitter/receiver back to the transmitter/receiver, wherein the reflector and the transmitter/receiver are arranged so as to sandwich a space that is measured.

8. The receiver according to claim 1, wherein the detector is a photodetector.

9. A receiver comprising:
a divider configured to divide an optical signal transmitted for detecting a detection target on a traveling path over a plurality of paths, including a first path, a second path, a third path, a fourth path, and a fifth path;
a detector configured to detect a received light intensity of the optical signal at a first position of the first path where the received light intensity becomes maximum, and at more than three positions out of a second position of the second path where the received light intensity increases when an optical axis of the optical signal is shifted in an upper right direction, a third position of the third path where the received light intensity increases when the optical axis of the optical signal is shifted in a lower right direction, a fourth position of the fourth path where the received light intensity increases when the optical axis is shifted in an upper left direction, and a fifth position of a fifth path where the received light intensity increases when the optical axis is shifted in a lower left direction;
a processor; and
a memory storing instructions executable by the processor to:
determine presence or absence of an optical axis shift and calculate an amount of the optical axis shift based on a change in a received light intensity ratio between the received light intensity of the optical signal at the first position and the received light intensity at the second, third, fourth, or fifth position.

10. The receiver according to claim 2, wherein the detector is a photodetector.

11. A detection method comprising:
dividing an optical signal over a plurality of paths including a first path and a second path;
receiving the optical signal at a first position of the first path where a received light intensity increases when an optical axis of the optical signal is shifted and at a second position of the second path where the received light intensity decreases when the optical axis is shifted;
calculating, by a processor, a received light intensity ratio based on the received light intensity at the first position and the received light intensity at the second position; and
determining, by the processor, presence or absence of an optical axis shift based on a change in the received light intensity ratio over time.

12. The method according to claim 11, the optical signal is divided using a beam splitter.

13. The method according to claim 11, wherein the optical signal is divided using a movable mirror.

14. The method according to claim 11, wherein the detector is a photodetector.

* * * * *